United States Patent [19]

Brooks et al.

[11] Patent Number: 4,568,673

[45] Date of Patent: Feb. 4, 1986

[54] COMPOSITIONS INHIBITING MURINE MXT DUCTAL CARCINOMA

[75] Inventors: Samuel C. Brooks, Orchard Lake; Jerome P. Horwitz, Oak Park, both of Mich.

[73] Assignee: Wayne State University, Detroit, Mich.

[21] Appl. No.: 591,500

[22] Filed: Mar. 20, 1984

[51] Int. Cl.$^4$ ............................................. A61K 31/56
[52] U.S. Cl. .................................................. 514/178
[58] Field of Search ......................... 424/243; 514/178

[56] References Cited

U.S. PATENT DOCUMENTS 3,377,362  4/1968  Cantrall et al. ................. 260/397.4
3,526,648  9/1970  Bertin et al. .................... 260/397.45
4,340,602  7/1982  Brooks ............................... 424/243

OTHER PUBLICATIONS

Rozhin et al., Cancer Res., 43:2611–2617, (Jun. 1983).
Rozhin et al., Proc. Am. Assoc. Cancer Res., 21:260, (1980).
Neeman et al., J. Med. Chem., 1983:465–469, (1983).
Utne et al., J. Org. Chem., 33:2469–2473, (1968).
Iyer et al, J. Org. Chem., 47:644, (1982).
Iyer et al, J. Med. Chem., 28:162, (1983).
Brooks et al., J. Toxic. and Environ. Health, 4:283–300, (1978).
Rozhin et al., J. Biol. Chem., 252:7214–7220, (1977).
Pack et al., Endocrinology, 95:1680–1690, (1974).

*Primary Examiner*—Elbert L. Roberts
*Attorney, Agent, or Firm*—John S. Roberts, Jr.

[57] ABSTRACT

A compound of the formula

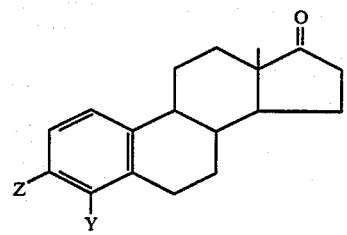

wherein Z is alkoxy of 1–4 carbon atoms or hydroxyalkoxy of 2–4 carbon atoms and Y is nitro, inhibiting the growth of murine ductal carcinoma (MXT mammary tumors).

3 Claims, 4 Drawing Figures

COMPOSITIONS INHIBITING MURINE MXT DUCTAL CARCINOMA

BACKGROUND OF THE INVENTION

This invention relates to the inhibition of hormone-dependent mammary tumors, such as those induced by 7/12-dimethylbenz(a)anthracene or transplantable ductal carcinoma (MXT murine type), by compounds known to be inhibitors of estrogen sulfotransferase.

Estrogen sulfotransferase inhibitors, such as 4-nitroestrone 3-methyl ether, are expected to prevent implantation of a blastocyst in the epithelial uterine lining of a pregnant female. Accordingly, these compounds may function as contragestative agents, Brooks U.S. Pat. No. 4,340,602.

A member of this group of compounds, 4-nitroestrone 3-methyl ether also has been found to inhibit the growth of hormone dependent mammary tumors, induced by 7,12-dimethylbenz(a)anthracene, Rozhin et al., Proc. Am. Assoc. Cancer Res., 21:260 (1980). It has been found that the utility of 4-nitroestrone 3-methyl ether is essentially limited to parenteral administration, particularly intraperitoneal or subcutaneous injection thereof.

It is an object of this invention to provide compounds which are active against hormone-dependent mammary tumors, other than those induced by 7,12-dimethylbenz-(a)anthracene and to provide compounds which are active when administered orally.

PRIOR ART STATEMENT

Brooks, in U.S. Pat. No. 4,340,602, herein incorporated by reference, has proposed that derivatives of 2- and/or 4-bromo- or nitro-estradiol or estrone, having an etherified hydroxyl function at the 3-position are active inhibitors of estrogen sulfotransferase activity. The active compounds should act to prevent implantation of a blastocyst in the epithelial uterine lining of a female mammal.

Cantrall et al (U.S. Pat. No. 3,377,362) indicate that 1-halo-3-methoxy-estra-1,3,5(10)-triene-17-one and related compounds have estrogenic, hypocholesteremic and protein anabolic activity.

Δ1,3,5(10)-Gonatrienes having an 11β-alkoxy substituent, wherein the 2-substituent is H, halogen or methyl; the 3-substituent is H, alkoxy or acyloxy; the 4-substituent is H, halo or lower alkyl; and the 17-substituent is =O or

are disclosed by Bertin et al., U.S. Pat. No. 3,526,648, as having estrogenic activity.

Pertinent literature references include:

Rozhin et al., "Effects of 4-Nitroestrone 3-Methyl Ether on Dimethylbenz(a)anthracene-induced Mammary Tumors," Cancer Res., 43:2611–2617 (June, 1983).

Rozhin et al., "Effect of an Inhibitor of Estrogen Sulfurylation, 4-Nitroestrone 3-Methyl Ether on Mammary Tumor Growth," Proc. Am. Assoc. Cancer Res., 21:260 (1980).

Neeman et al., "Modified Steroid Hormones. 7. 4-Fluoro-17β-estradiol: Carbon-13 Nuclear Magnetic Resonance, Crystal and Molecular Structure, and Biological Activity," J. Med. Chem., 1983:465–469 (1983).

Utne et al., "The Synthesis of 2- and 4-Fluoroestradiol," J. Org. Chem., 33:2469–2473 (1968).

Iyer et al., J. Org. Chem., 47:644 (1982) and J. Med. Chem., 28:162 (1983).

Brooks et al., "Role of Sulfate Conjugation in Estrogen Metabolism and Activity," J. Toxic. and Environ. Health, 4:283–300 (1978).

Rozhin et al., "Studies on Bovine Adrenal Estrogen Sulfotransferase: II. Inhibition and Possible Involvement of Adenine-estrogen Stacking," J. Biol. Chem., 252:7214–7220 (1977).

Pack et al., "Cyclic Activity of Estrogen Sulfotransferase in the Gilt Uterus," Endocrinology, 95:1680–1690 (1974).

SUMMARY OF THE INVENTION

This invention relates to a composition which inhibits the growth of hormone dependent MXT mammary tumors, comprising a compound of the formula

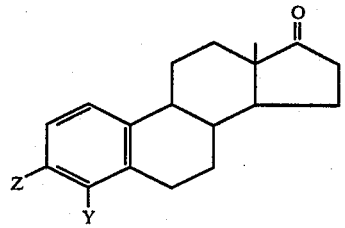

wherein Z is alkoxy of 1–4 carbon atoms or hydroxyalkoxy of 2–4 carbon atoms and Y is nitro, in admixture with a pharmaceutically acceptable carrier.

This invention further relates to a method of inhibiting the growth of MXT murine ductal carcinoma by administering to an animal being treated an amount of one of the foregoing compounds, effective to inhibit growth of MXT ductal carcinoma.

DETAILED DESCRIPTION OF THE INVENTION

Figure 1:
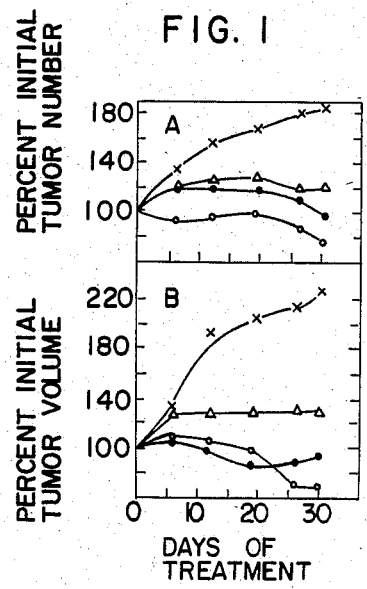
In FIG. 1–3 are shown the effect of 4-nitroestrone 3-methyl ether on the growth of murine mammary tumors, induced by 7,12-dimethylbenza(a)anthracene.

Compounds of this invention are ethers of the 3-hydroxy function of 4-nitroestrone. Therefore, in the formulas of this disclosure, Z is alkoxy of 1–4 carbon atoms or hydroxyalkoxy of 2–4 carbon atoms. This group of ethers includes methoxy, ethoxy, propoxy and butoxy as well as hydroxyethoxy, hydroxypropoxy and hydroxybutoxy compounds, including the various possible isomers.

When the compounds disclosed are administered subcutaneously, preferred compounds are the 3-methoxy or 3-(γ-hydroxypropoxy) compound. For oral administration the 3-(γ-hydroxypropoxy) compound is preferred.

Synthesis and Evaluation Section

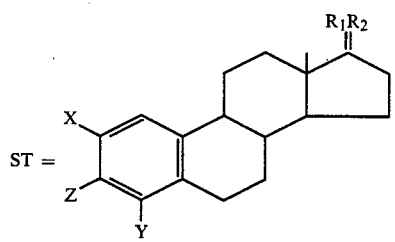

In the specification, ST represents an estra-1,3,5(10)-triene residue and substituents X, Y, Z, R, and $R_2$ are as indicated in each case.

4-Fluoroestra-1,3,5(10)-trien-17β-ol was synthesized from 4-fluorostrone (ST; Z=OH, Y=F, $R_1+R_2$=O) by conversion to the 3-O-(1-phenyl-1H-tetrazol-s-yl)ether, reduction with sodium borohydride to the 17β-ol and hydrogenolysis:

ST; Z = OH, Y = F, $R_1 + R_2$ = O

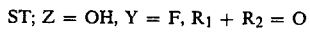 5-chloro-1-phenyl-1H—tetrazole/acetone/potassium carbonate

ST; Z = OT, Y = F, $R_1 + R_2$ = O

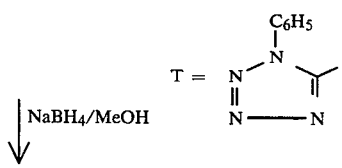

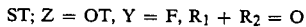 NaBH$_4$/MeOH

ST; Z = OT, Y = F, $R_1$ — βOH, $R_2$ = H

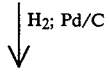 H$_2$; Pd/C

ST; Z = H, Y = F, $R_1$ = βOH, $R_2$ = H

5-Chloro-1-phenyl-1H-tetrazole, used for the etherification of a 3-hydroxyl group and subsequent hydrogenolysis is disclosed by Musliner et al., "The Replacement of Phenolic Hydroxyl Groups by Hydrogen," *J. Am. Chem. Soc.*, 88:4271-3 (1966).

Oxidation of 4-fluoroestra-1,3,5(10)-trien-17β-ol (ST; Z=H, Y=F, $R_1$=βOH, $R_2$=H) with chromium trioxide in sulfuric acid gave 4-fluoroestra1,3,5(10)-trien-17-one ($R_1+R_2$=O).

A readily separable mixture of 2- and 4-nitroestrone is obtained by nitration of estrone (ST; Z=OH, $R_1+R_2$=O) with a stoichiometric amount of nitric acid in glacial acetic acid. See, generally, Werbin et al., *J. Biol. Chem.*, 223:651 (1965); Krachy, et al., *J. Am. Chem. Soc.*, 79:754 (1957); Pickering, et al., Ibid, 80:680 (1958); and Tomson, et al., *J. Org. Chem.*, 24:2056 (1959).

4-Aminoestra-1,3,5(10)-trien-17β-ol was synthesized, starting from 4-nitroestrone. This was converted to 4-nitroestrone 3-O-(trifluoromethyl)sulfonate (ST; Z=CF$_3$SO$_2$O, Y=NH$_2$, $R_1$=17β-OH, $R_2$=H), which was treated with hexadecyltributylphosphonium bromide/sodium borohydride to 4-nitroestra-1,3,5(10)-trien-3,17-diol 3-O-(trifluoromethyl)-sulfonate (ST; Z=CF$_3$SO$_2$O, Y=NO$_2$, $R_1$=17β-OH) and reduced by hydrogenation.

ST; Z = OH, Y = NO$_2$, $R_1 + R_2$ = O

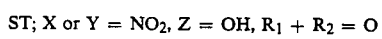 CF$_3$SO$_2$Cl/Et$_3$N

ST; Z = CF$_3$SO$_2$O, Y = NO$_2$, $R_1 + R_2$ = O

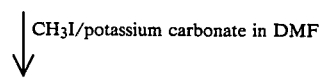 C$_{16}$H$_{33}$(C$_4$H$_9$)$_3$$\overset{+\,-}{P}$Br/NaBH$_4$

ST; Z = CF$_3$SO$_2$O, Y = NO$_2$, $R_1$,$R_2$ = H, OH

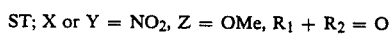 H$_2$ - Pd/C

ST; Z = H, Y = NH$_2$, $R_1$ = βOH, $R_2$ = H

Phenyl trifluoromethanesulfonate is disclosed by Yagupol'skii et al., "Aryl Trifluoromethanesulfonates," Institute of Organic Chemistry, Academy of Sciences of the Ukranian SSR. Translated from *Zhurnal Organicheskoi Khimii*, 7:996–1001 (1971). Hydrogenolysis of phenol or enols using perfluorosulfonates is shown by L. R. Subramanian et al., "Perfluoroalkane Sulfonic Esters, Methods of Preparation and Applications in Organic Chemistry," *Synthesis*, 85–125 (1982).

An alternative route to 4-fluoroestra-1,3,5(10)-trien-17-one was conversion of 4-aminoestra-1,3,5(10)-trien-17β-ol to a corresponding diazonium fluoroborate derivative, which was decomposed to 4-fluoroestra-1,3,5(10)-trien-17β-ol. Oxidation of the latter with chromium trioxide in sulfuric acid gave the corresponding 17-ketone.

Replacement of an amino group at the 3-position of selected steroidal compounds by a fluoro is shown in Morrow et al., "The Trienes," *J. Med. Chem.*, 9:249–51 (1966).

2-Amino- and 4-aminoestrone are obtained by reduction of the corresponding nitroestrone with sodium hydrosulfite (Na$_2$S$_2$O$_4$) in actone-aqueous alkali solution by the technique of Kratchy et al., supra.

2-Fluoro- and 4-fluoroestrone are prepared in accordance with Utne, supra.

Chloro-, bromo- and iodoestrones (X=Cl, Br, I or Y=Cl, Br, I; Z=OH, $R_1+R_2$=O) is accomplished starting from 2-nitro or 4-nitroestrone by treatment with methyl iodide/potassium carbonate to give the 3-O-methyl ether, which is reduced catalytically using W-2 Raney nickel or chemically using sodium hydrosulfite to a corresponding amino compound. Aminoestrone 3-O-methyl ethers are converted to corresponding halo compounds by Sandmeyer reaction.

ST; X or Y = NO$_2$, Z = OH, $R_1 + R_2$ = O

↓ CH$_3$I/potassium carbonate in DMF

ST; X or Y = NO$_2$, Z = OMe, $R_1 + R_2$ = O

↓ reduction

ST; X or Y = NH₂, Z = OMe, R₁ + R₂ = O

↓ NaNO₂/Cu hal, H hal
    hal = Cl, Br, I

ST; X or Y = Cl, Br or I, Z = OME
R₁ + R₂ = O

↓ demethylation

ST; X or Y = Cl, Br or I, Z = OH
R₁ + R₂ = O

Methylation of the 3-hydroxyl function can be done by the method of Tomson et al., supra.

Catalytic reduction can be done by the method of Tomson et al., supra, or that of Utne et al., supra. Chemical reduction can be done according to Kratchy et al., supra.

The Sandmeyer reaction can be done in accordance with Tomson et al., supra, or Sweet et al, *J. Med. Chem.*, 44:2296 (1979).

Demethylation of a corresponding 3-O-methyl ether is done with boron tribromide, Rice, *J. Med. Chem.*, 20:164 (1977); with trimethylsilyl chloride/sodium iodide in acetonitrile, Jung et al., *J. Org. Chem.*, 42:3761 (1977) or Olah et al., *J. Org. Chem.*, 44:1247 (1979); with silicon tetrachloride/sodium iodide in dichloromethane/acetonitrile, Bhatt et al., *Synthesis* (1982) at 1048; or with sodium ethylmercaptide in dimethylformamide, Fentrill et al., *Tetrahedron Lett.*, (1970) at 1327.

3-O-(Hydroxyalkyl)ethers of nitroestrone were prepared by treating 2-nitroestrone with 2-bromoethanol or 3-bromopropanol in an aprotic dipolar solvent, e.g., DMF, in the presence of potassium carbonate or sodium hydride, Iyer et al., supra. For example, 4-nitroestrone was converted to the corresponding ethers:

ST; X = H, Y = NO₂, Z = OH, R₁ + R₂ = O

↓ HOCH₂(CH₂)ₙBr, NaH/DMF    n = 1,2

ST; X = H, Y = NO₂, Z = O(CH₂)ₙ₊₁OH,
R₁ + R₂ = O

It is proposed to prepare 3-O-(2-hydroxypropyl)ethers from 2- and 4-substituted estrones by protecting the 17-carbonyl group as a 17-ethandiyl acetal by reaction with ethylene glycol in DMF; etherifying the 3-hydroxyl group with chloroacetone in the presence of potassium carbonate; reducing the keto-function with sodium borohydride and deblocking the C-17 ketone with a mineral acid:

ST; Z = OH, R₁ + R₂ = O

↓ HOCH₂CH₂OH, DMF/HCl

ST; Z = OH, R₁, R₂ = OCH₂CH₂O

↓ CH₃COCH₂Cl, K₂CO₃,
    acetone

ST; Z = OCH₂COCH₃, R₁, R₂ = OCH₂CH₂O

↓ (1) NaBH₄
   (2) Mineral acid

ST; Z = OCH₂CHOHCH₃, R₁ + R₂ = O

Ethers, other than the O-methyl ether of 2- or 4-substituted estrone compounds, are prepared by reaction between an estrone (Z=OH, R₁+R₂=O) and a corresponding alkyl halide, e.g., CH₃(CH₂)ₙBr, wherein n=1-3 or CH₃(CH₂)ₙCHBrCH₃, wherein n=1-3; a corresponding halocycloalkane, CH₂—(CH₂)ₙCHBr, wherein n=3 or 4; or a 3-O-allyl or benzyl halide. The reaction is carried out as for the rections using 2-bromoethanol or 2-bromopropanol.

4-O-(4-Hydroxybutyl)ethers of 2- and 4-substituted estrones employ a 17-ketal as above. The 3-hydroxyl is etherified with 1-bromo-3-butene and the O-homoallylic ether subjected to hydroboration with 9-borobicyclononane, followed by in situ treatment with alkaline hydrogen peroxide to give anti-Markovnikov addition and a resulting 4-hydroxybutyl ether, Zweifel et al., *Organic Reactions,* 1:13 (1963).

ST; Z = OH, R₁ + R₂ = OCH₂CH₂O

↓ CH₂=CHCH₂CH₂Br, K₂CO₃/DMF

ST; Z = OCH₂CH₂CH=CH₂,
R₁ + R₂ = OCH₂CH₂O

↓ (1) 9-borabicyclononane
   (2) H₂O₂
   (3) H₃O⁺

ST; Z = OCH₂CH₂CH₂CH₂OH, R₁ + R₂ = O

The compounds of this invention were evaluated for inhibitory activity against murine hormone-dependent mammary tumors of the MXT type or of the type induced by 7,12-dimethylbenz(a)anthracene by methods cited above.

Due to their tumor inhibiting activity, the compounds of this invention are useful for treating hormone-dependent mammary tumors in human and verterinary medicine.

The compounds of this invention can be employed in admixture with conventional excipients, i.e., pharmaceutically acceptable organic or inorganic carrier substances suitable for parenteral, enteral or topical application, which do not deleteriously react with the active compounds.

Suitable pharmaceutically acceptable carriers include but are not limited to water, salt solutions, alcohols, vegetable oils, polyethylene glycols, gelatine, lactose, amylose, magnesium stearate, talc, silicic acid, viscous parafin, perfume oil, fatty acid monoglycerides and diglycerides, pentaerythritol fatty acid esters, hydroxymethyl cellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for incluencing osmotic pressure, buffers, coloring, flavoring and/or aromatic substance, which do not deleteriously interact with the active compounds.

For parenteral application, solutions are particularly suitable, including oily or aqueous solutions, suspensions, emulsions, implants or suppositories. Ampoules are convenient unit dosages.

It will be understood that preferred dosages of the active compounds used will vary according to the specific compound being used, the particular compositions formulated, the mode of application, and the particular organism being treated. Optimal application rates for a given set of conditions can be ascertained by those skilled in the art using conventional dosage determination tests in view of the above guidelines.

DESCRIPTION OF MOST PREFERRED EMBODIMENT

In a most preferred embodiment, 4-nitroestrone b 3-O-(2-hydroxypropyl)ether will be administered orally.

Without further elaboration, it is believed that one skilled in the art can, using the preceding description, utilize the present invention to its fullest extent. The following preferred specific embodiments are therefore to be construed as merely illustrative and not limitative of the remainder of the specification and claims in any way whatsoever.

EXAMPLE 1

4-Fluoroestrone 3-O-(1-Phenyl-1H-tetrazol-5-yl)Ether

A solution of 4-fluoroestrone (210 mg, 0.73 mmol), prepared according to the method of Utne et al., supra, and 5-chloro-1-phenyl-1H-tetrazole (130 mg, 0.73 mmol) in 30 ml of anhydrous acetone containing anhydrous potassium carbonate (210 mg, 1.46 mmol) and protected from moisture was heated under reflux for 24 hr. The reaction mixture ws filtered through a pad of Celite and the filtrate was evaporated to dryness. The residue was dissolved in dichloromethane and the solution was washed first with (2×5 ml) 10% NaOH and then with water. The solution was dried over sodium sulfate and evaporated to dryness. The residue was crystallized from absolute ethanol to produce fine, colorless needles of 4-fluoroestrone 3-O-(1-phenyl-1H-tetrazol-5-yl) ether (250 mg, 79% yield): mp 161°–163° C.; $^1$H NMR δ 7.89–7.54 (m, 5, $C_6H_5$) 7.39, 7.19 (dd, 2, aromatic $H_1$, $H_2$), 2.92–1.45 (m, 15) 0.93 (s, 3, $C_{18}CH_3$); Ir (KBr) 1720 cm$^{-1}$ ($C_{17}$ C=O).

Anal. Calc'd for $C_{25}H_{25}FN_4O_2$: C, 69.42; H, 5.83; N, 12.96; F, 4.39. Found: C, 69.36; H, 5.83; N, 12.78; F, 4.51.

EXAMPLE 2

4-Fluoroestra-1,3,5(10)-trien-17β-ol (a) To a solution of 4-fluoroestrone 3-O-(1-phenyl-1H-tetrazol-5-yl)ether as prepared in Example 1 (220 mg, 0.5 mmol) in methanol (75 ml) was added, at room temperature with stirring, a solution of sodium borohydride (120 mg, 1.5 mmol) in 2 ml of 25% aqueous methanol. The resulting mixture was stirred for 45 min. The solvents were removed under reduced pressure and the residue, dissolved in 10 ml dichloromethane, was washed with dilute (2%) HCl. The solution was dried over $Na_2SO_4$ and evaporated to dryness to yield a colorless foam, 4-fluoroestra-1,3,5(10)-trien-17-diol-3-O-(1-phenyl)-1H-tetrazole-5-yl)ether (260 mg, 74% yield). This appeared as a single spot on TLC and in 95% dichloromethane-5% methanol solvent system. The infrared spectrum had no 17-keto absorption.

(b) Unrecrystallized ether as prepared in (a) (160 mg, 0.37 mmol), was dissolved in 50 ml of EtOH containing 40 mg (25% by wt.) of 10% Pd/C and was hydrogenolyzedfor 18 hr. in a Parr apparatus pressurized to 53 psi. The solution was filtered with Celite and evaporated to dryness. The residue was dissolved in dichloromethane and washed first with (2×10 ml) 10% NaOH and then with water. The solution was dried over sodium sulfate to reveal the presence of three products on TLC using 95% dichloromethane-5% methanol. The slowest moving material was separated on preparative TLC with the same solvent system and, on evaporation, gave 4-fluoroestra-1,3,5(10)-trien-17β-ol as a foam, wt. 50 mg, 49% yield. $^1$H NMR 7.15–6.79 (m, 3, aromatic), 3.73 (t, 1, $H_{17\alpha}$), 2.84–1.26 (m, 16) 0.78 (s, 3, $C_{18}CH_3$); mass spectrum: m/z 275 (M$^+$ + 1).

Anal. Calc'd for $C_{18}H_{23}FO$: C, 78.79, H, 8.45; F, 6.92. Found: C, 78.61; H, 8.58; F, 7.06.

EXAMPLE 3

4-Fluoroestra-1,3,5(10)-trien-17-one

To a solution of 4-fluoroestra-1,3,5(10)-trien-17β-ol (100 mg, 0.36 mmol) in 1.5 ml of acetone at 0° C. was added, dropwise with stirring, a solution of 95 ml of 8N chromium trioxide in 8N sulfuric acid. After approximately 5 min. the reaction mixture was poured into 75 ml of ice water and the solids were collected. The filter cake was stirred with methanol. The inorganic salts were removed and the filtrate was evaporated to dryness to give the crude product, 4-fluoroestra-1,3,5-(10)-trien-17-one as a tan solid. The latter was crystallized from ether-petroleum ether (30°–60°) as a colorless solid (60 mg, 61% yield), mp 139°–141° C. Ir (KBr)cm$^{-1}$ 1724 ($C_{17}$ C=O), 1230 (aryl fluoride); $^1$H NMR δ 7.21–6.81 (m, 3, $H_1$, $H_2$, $H_3$ aromatic) 2.91–1.54 (m, 15), 0.92 (s, 3, $C_{18}CH_3$).

Anal. Calc'd. for C, 79.38; H, 7.77; F, 6.98. Found: C, 79.53; H, 7.76; F, 7.13.

EXAMPLE 4

4-Nitroestrone 3-O-(trifluoromethyl)sulfonate

To a solution of 4-nitroestrone (630 mg, 2 mmol) in 50 ml dry acetone containing 350 ml (2.5 mmol) of triethylamine was added 265 ml (2.5 mmol) of trifluoromethanesulfonyl chloride and the reaction mixture, protected from moisture, was heated under reflux for 3 hr. The solvent was evaporated to dryness and residue was dissolved in 100 ml of dichloromethane. The solution was washed and dried over sodium sulfate. The filtered solution was evaporated to dryness and the residue, 4-nitroestrone-3-O-(trifluoromethyl)sulfonate, which had a single spot on TLC using 99% dichloromethane-1% methanol, was crystallized from 2-propanol in the form of yellow needles, wt. 700 mg, (78% yield), mp 198°-202° C. IR (KBr) cm$^{-1}$ 1740 ($C_{17}$ C=O), 1545, 1370 ($NO_2$), 1430, 1220 (—$OSO_2$—). $^1$H NMR 7.53, 7.28 (dd, 2, aromatic $H_1$, $H_2$), 3.00–1.2 (m, 15), 0.93 (s, 3, $C_{18}CH_3$).

Anal. Calc'd, for $C_{19}H_{20}NO_6SF_3$: C, 51.00; H, 4.51; N, 3.13; S, 7.17; F, 12.74. Found: C, 15.13; H, 4.66; N, 3.03, S, 6.93; F, 12.56.

EXAMPLE 5

4-Nitroestra-1,3,5(10)-triene-3,17-diol 3-O-(Trifluoromethyl)-Sulfonate

To a solution of 230 mg (0.5 mmol) of 4-nitroestrone 3-O-(trifluoromethyl)sulfonate in 230 ml of toluene, containing hexadecyltributylphosphonium bromide (26 mg, 0.05 mmol) was slowly added a solution of sodium borohydride (60 mg 1.5 mmol) in 150 ml of water and the resulting mixture was stirred at room temperature for 3 hr. Additional (10 ml) toluene was added and the organic layer was separated and then washed with water. The toluene solution was dried over sodium sulfate and then evaporated to an oily residue. This gave a colorless foam of 4-nitroestra-17-diol 3-O-(trifluoromethyl)sulfonate (184 mg, 82% yield) on evaporation from ether. Ir (KBr) cm$^{-1}$ 1540, 1365 ($NO_2$), 1430, 1230 (—$OSO_2$—). $^1$H NMR δ7.52, 7.26, (dd, 2, aromatic $H_1$, $H_2$), 3.68 (t, 1.17H), 2.88–1.28 (m 16), 0.80 (s, 3, $C_{18}CH_3$).

Anal. Calc'd. for $C_{19}H_{22}NO_6SF_3$: C, 50.77; H, 4.93; N, 3.12; S, 7.14; F, 12.68. Found: C, 50.58; H, 5.03; N, 3.00; S, 6.95; F, 12.79.

EXAMPLE 6

4-Aminoestra-1,3,5(10)-trien-17β-ol

A solution of 4-nitroestra-1,3,5(10)-trien-3,17-diol 3-O-triflate (2.13 g, 4.74 mmol) in 100 ml of methanol containing triethylamine (6.60, 4.8 mmol) and 10% Pd/C (430 mg. 20% by weight) was hydrogenated in a Parr apparatus at 16 psi for 5 hr. TLC using 95% dichlormethane 1% methanol showed one major product and 3 minor constituents. The reaction mixture was filtered through Celite and the filtrate was evaporated to dryness. The residue was dissolved in excess dichloromethane and the solution was washed with water. The extract was dried over sodium sulfate and filtered. The filtrate was evaporated to dryness. The residue crystallized from methanol as a cluster of colorless needles of 4-aminoestra-1,3,5(10)-trien-17β-ol; wt. 320 mg. (25% yield), mp 189°-192° C. Mass Spectrum: m/z 271 (M+), 237 (M—$H_2O+NH_2$). $^1$H NMR 7.23–6.51 (m, 3, $H_1$, $H_2$, $H_3$ aromatic) 3.71–3.45 (t, 1, 17H), 2.57–1.23 (m, 18), 0.876 (s, 3, $C_{18}CH_3$).

Anal. Calc'd. for $C_{18}H_{25}NO$: C, 79.66; H, 9.28; N, 5.16. Found: C, 79.72; H, 9.11; N, 4.97.

EXAMPLE 7

4-Fluoroestra-1,3,5(10)-trien-17β-ol

A solution of (230 mg, 0.85 mmol) 4-aminoestra-1,3,5(10)-trien-17β-ol in 4.6 ml of ethanol containing 2.3 ml of 48% hydrofluoric acid, was cooled to 0° C. and maintained at this temperature with stirring under dropwise addition of an aqueous solution (230 ml) of sodium nitrite (60 mg, 0.88 ml). After 1 hr. of stirring at 0°, the reaction mixture was first treated with a few crystals of urea and then poured into 150 ml of ether. The product, a colorless solid, was collected and dried at room temperature in vacuo over $P_2O_5$ for 24 hr., wt. 220 mg (70% yield).

The diazonium fluoroborate derivative (160 mg, 0.59 mmol) was suspended in 25 ml of a mixture of dry xylenes and heated under reflux for 3 hr. The cooled suspension was filtered and the filtrate, which showed the presence of three products, including 4-fluoroestra-1,3,5(10)-trien-17β-ol, by TLC analysis using 100% dichloromethane, was evaporated to dryness. The residue was subjected to preparative TLC using the same solvent system and the desired product, 4-fluoroestra-1,3,5(10)-trien-17β-ol, was isolated as a foam (wt. 60 mg, 37% yield). The latter, on (mass and $^1$H NMR) spectral analyses, was identical in all respects with a sample obtained from Example 2.

EXAMPLE 8

Effects of 4-Nitroestrone 3-Methyl Ether (ST; Y=$NO_2$, Z=OMe, $R_1+R_2$=O), on Mammary Tumors Induced by Dimethylbenz(a)anthracene Chemicals and Reagents. Estrone, 17β-estradiol 3-benzoate, estrone sulfate, aryl sulfatase (EC 3.1.6.1), β-glucuronidase (EC3.2.1.31), 7,12-dimethylbenz(a)anthracene (DMBA), and 5-fluorouracil were obtained from Sigma Chemical Co. (St. Louis, MO). 4-Nitroestrone 3-methyl ether, 4-nitroestrone, and 2,4-dinitroestrone were synthesized by the procedures of Tomson et al., supra.

Tamoxifen (free base) and nafoxidine (U-11, 100A) were supplied by Drs. D. H. McCurdy of Stuart Pharmaceuticals (Division of ICI Americas, Inc.) and J. Babcock of the Upjohn Co. (Kalamazoo, MI), respectively. Adriamycin (doxorubicin-HCl) was purchased from Adria Laboratories, Inc., Columbus, Ohio.

Animals. Virgin female Sprague-Dawley rats (The Charles River Co., Wilmington, MA) were housed 4 to 6/cage in a light (12 hr/day)—and temperature (24°)—controlled room and given a diet of Wayne Lab-Blox laboratory chow (Allied Mills, Inc., Chicago, IL) and tap water ad libitum. At 50 days of age, rats were intubated with DMBA (10 mg/100 g body weight) dissolved in sesame oil (20 mg/ml). Beginning at Day 45 after intubation, all animals were weighed and palpated once per week. Tumor volumes were calculated by measuring 2 diameters with a caliper and the third dimension with a ruler, then by substituting values:

Volume (cu cm) = $\pi$ 1/6 abc where a, b, and c are the 3 different diameters of the tumor. The agreement of the in vivo tumor volume and measurements of excised tumors identified as necropsy was 95 to 99%. When about 75% of rats had palpable tumors (81 to 92 days after intubation), the animals were randomized, excluding rats with tumors larger than 2.00 ml and rats with more than 5 tumors/animal. The mean initial tumor volumes in control and treated groups ranged between 0.4 and 0.9 cu cm over the various experiments. When necessary, ovariectomy (ether anesthesia) was performed on the first or second day after the initiation of the study. The significance of difference between treatment groups was examined by Student's t test.

Estrogen derivatives (>99% pure by thin-layer chromatography) and the nonsteroidal antiestrogens were injected s.c. daily (Monday to Friday). After distribution in SSV (steroid-suspending vehicles, 0.9% NaCl solution with 0.5% sodium carboxymethyl-cellulose-7, 0.4% polysorbate; and 0.9% benzylalcohol, obtained from the National Cancer Institute), the steroids (20 mg/ml) were administered at 0.12 to 54 mg/kg body weight. The suspension was sonicated before use to achieve uniform distribution. Tamoxifen, nafoxidine, and 17β-estradiol 3-benzoate were dissolved in a minimum amount of 100% ethanol and added to sesame oil, and the ethanol was evaporated under a stream of nitrogen to give a final concentration of 1 mg/ml oil. 17β-Estradiol 3-benzoate was dissolved directly in sesame oil to a concentration of 2.5 mg/ml; 5 fluorouracil was dissolved in water (25 mg/ml), and Adriamycin was dissolved in 0.9% NaCl solution. The control group was given injections of SSV or sesame oil alone.

The toxicity of all antitumor agents was determined by comparing body weights of treated and control animals.

Postmortem Examination and Histopathology of Tumors. Rats were selected for colchicine injections (2 mg/kg body weight) 2 hr prior to necropsy to obtain an accurate measurement of mitotic indices of tumors. Animals were sacrificed with $CO_2$ gas or bled to death via the abdominal aorta. Tumors and tissues were removed and preserved in 10% neutral buffered formalin for histopathological examination. Gross anomalies of abdominal, thoracic, and cranial cavities were recorded. Uteri were removed, trimmed, and weighed fresh. Ovaries, adrenals, and pituitaries were trimmed and weighed after fixation.

Histopathological observations on hematoxylin and iosin-stained tumor and organ sections were performed, and comparisons between the control and treated groups were carried out using computer analysis. The microscopic parameters used to judge the degree of anaplasia in DMBA-induced mammary neoplasms, when treated animals were compared to controls, were: (a) the type of epithelium or mammary tissue involved; (b) the degree of encapsulation of the neoplasm; (c) the number of mitotic figures observed; (d) the extent of stroma invasions of the neoplastic epithelium; (e) the severity of lymphocytic infiltration of the neoplasms; and (f) the regressive, degenerative, or vacuolative changes in the neoplastic epithelium. These criteria are suggested by Boylan et al., "Morphology, growth characteristics and estrogen binding capacity of DMBA-induced mammary tumors from ovariectomized rats," Br. J. Cancer, 35:602–609 (1977); Gullino et al., "Physiopathological characteristics of hormone dependent tissue," J. Natl. Cancer Inst., 49:1333–1348 (1972); Haslam et al., "Histopathogenesis of 7,12-dimethylbenz(a)anthracene induced rat mammary tumors," Proc. Natl. Acad. Sci. U.S.A., 74:4020–4024 (1977); Russo, "Pathogenesis of mammary carcinomas induced in rats by 7,12-dimethylbenz(a)anthracene," J. Natl. Cancer Inst., 49:435–445 (1977) and Strettony et al., "Spontaneous regression of induced mammary tumors in rats," Br. J. Cancer, 17:85–89 (1973). Histological examination was performed on all mammary tumors.

Results. In a series of tests using 7–10 Sprague-Dawley rats/group, subcutaneous injections of 24 mg/kg of body weight of an estrogen analog being evaluated were given for 35 days. The estrogen analogs selected were known to be superior estrogen sulfotransferase inhibitors, Rozhin et al., J. Biol. Chem., 252:7214–7220 (1977).

In the table below, the mean values are the mean ±S.D. The following results were obtained:

| Estrogen analog injected | Mean tumor volume (cu cm) | Mean tumor no. (no. tumors/rat) |
|---|---|---|
| None | 1.48 ± 2.09 | 3.30 ± 2.60 |
| 2,4-Dibromoestrone 3-methyl ether | 1.24 ± 1.07 | 4.26 ± 2.51 |
| 2,4-Dinitroestrone | 1.14 ± 1.37 | 2.90 ± 1.67 |
| 4-Nitroestrone | 0.75 ± 0.10 | 1.95 ± 2.60 |
| 4-Nitroestrone 3-methyl ether | 0.05 ± 0.05 | 1.35 ± 0.40 |

In the table p values, when compared to those of the control tumors, were <0.05. The results for the 2,4-dibromoestrone 3-methyl ether, 2,4-dinitroestrone, and 4-nitroestrone treatments were therefore insignificant.

EXAMPLE 9

Effect of the Level of 4-Nitroestrone 3-Methyl Ether on DMBA-induced Mammary Tumors in Rats Mammary tumors were induced in Sprague-Dawley rats (14–15 rats/group) as in Example 11. The rats were treated with 4-nitroestrone 3-methyl ether at various dosage levels and tumor behavior was followed for 30 days of treatment. Results are shown in FIG. 1. In the upper part (A), the vertical axis represents the percent of number of tumor, compared to the initial number. In the lower part (B), the vertical axis represents percent of tumor volumes, compared to a corresponding initial volume. The horizontal axis represents days of treatment.

The dosage levels are represented by the following symbols:

x: none
Δ: 12 mg/kg of body weight
o: 24 mg/kg of body weight
●: 54 mg/kg of body weight As shown on the figure, insignificant inhibition of tumor growth was observed for the 12 mg/kg of body weight. At the end of 30 days' treatment, experimental values for tumor number diffused from those of controls at the following doses: 24 mg/kg, $p<0.01$; 54 mg/kg, $p<0.05$. Values for tumor volume differed from those of controls at the following doses: 24 mg/kg, $p<0.02$; 54 mg/kg, $p<0.05$.

Accordingly, daily doses of 4-nitroestrone 3-methyl ether exceeding 24 mg/kg of body weight give significant inhibition of DMBA-induced mammary tumors in rats.

EXAMPLE 10

Figure 2:
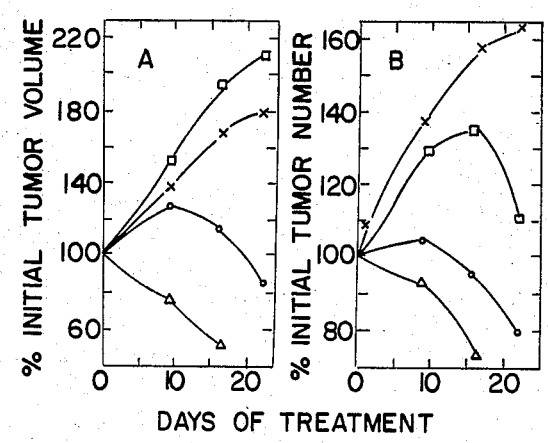

Comparison of 4-Nitroestrone 3-Methyl Ether with Other Inhibitors of DMBA-induced Mammary Tumors Each group of 10 rats with DMBA-induced mammary tumors in accordance with Example 11 was treated with results as shown in FIG. 2 for the following dosages of treating agents:

x: control
□: 4-nitroestrone 4 mg/kg of body weight
o: 4-nitroestrone 3-methyl ether 24 mg/kg
Δ: 17β-estradiol 3-benzoate 1.6 mg/kg In these experiments, samples of tumors and organs were taken for histopathological observations at the time when treated tumors were responding to the various agents but before the treated group tumors had disappeared or the control grouup tumors became necrotic. This timing was selected so that specimens could be obtained while there was still enough tumor tissue, and the resulting histopathological preparations could be examined for the effects of the treatments. For this reason, 17β-estradiol 3-benzoate treatment was terminated on Day 16, and the remaining groups were treated for 22 days.

A pharmacological level of 17β-estradiol 3-benzoate was most effective in bringing about the regression of DMBA-induced mammary tumors (FIG. 2). However, 4-nitroestrone 3-methyl ether was quite effective after 22 days as shown both by diminution of tumor growth and by appearance of the tumors in comparison to the tumors of the animals in the control group.

After 16 days of treatment with 17β-estradiol 3-benzoate, the tumor volume and number differed from those of controls ($p<0.02$) in both cases. Following 22 days of treatment with 4-nitroestrone 3-methyl ether, the tumor volume and number both differed from those of controls ($p<0.05$). There was no significant change in these values in those rats given injections of 4-nitroestrone.

EXAMPLE 11

Effect of Treatment on Rat Body Weights and Organ Weights and Histopathological Characteristics of Tumors Studies were done as in Example 10, generally for 13 days. The ovariectomized animals were removed from the study at Day 9 and the 17β-estradiol benzoate group at Day 16 so as to do histopathological studies.

The changes in initial tumor volume noted when each treatment was terminated were: control, 173%; ovariectomy, 34%; 4-nitroestrone 3-methyl ether, 85%; 4-nitroestrone, 212%; tamoxifen, 131%; tamoxifen plus 4-nitroestrone 3-methyl ether, 70%; Adriamycin plus 5-fluorouracil, 155%; and 17β-estradiol 3-benzoate, 51%.

Body and organ weights and prolactin levels are given in Table 1 and histopathological characteristics for corresponding treatment in Table 2.

Most of the treatments resulted in disappearance of adenocarcinomas with little effect on fibroadenomas. Only 4-nitroestrone 3-methyl ether caused a decrease in adenocarcinomas but an increase in fibroadenomas and an overall decrease in total tumors.

TABLE 1

| Treatment | Body wt (g) | Organ wt (mg) | | | | Prolactin levels[a] (ng/ml) |
| --- | --- | --- | --- | --- | --- | --- |
| | | Uterus | Ovaries | Adrenals | Pituitary | |
| Control | 286 ± 28[b] | 612 ± 120 | 72 ± 11 | 77 ± 18 | 17 ± 3 | 139 ± 26 |
| Ovariectomy | 295 ± 20 | 226 ± 65 | | 60 ± 12 | 15 ± 1 | 47 ± 30 |
| 4-Nitroestrone 3-methyl ether[c] | 269 ± 36[d] | 850 ± 21[e] | 32 ± 11[e] | 71 ± 22 | 17 ± 3 | 220 ± 150 |
| 4-Nitroestrone[c] | 226 ± 26 | 861 ± 378 | 34 ± 6[e] | 62 ± 12 | 16 ± 2 | 108 ± 73 |
| Tamoxifen[f] | 262 ± 15 | 327 ± 44[g] | 32 ± 6[e] | 58 ± 10 | 13 ± 2 | 155 ± 67 |
| Tamoxifen + 4-nitroestrone 3-methyl ether[f] | 270 ± 17 | 398 ± 42 | 30 ± 5[e] | 62 ± 9 | 14 ± 1 | 194 ± 89 |
| Adriamycin + 5-fluorouracil[h] | 271 ± 23 | 590 ± 206 | 75 ± 9 | 68 ± 7 | 17 ± 2 | 86 ± 77 |
| Estradiol-benzoate[c] | 272 ± 24 | 1090 ± 764 | 73 ± 37 | 53 ± 7 | 36 ± 8[e] | 535 ± 206[e] |

[a]Dr. R. Gala, Department of Physiology, Wayne State University School of Medicine, Detroit, MI, performed the radioimmunoassays on blood serum prolactin. The procedure followed the double antibody technique using anitserum prolactin from pituitary culture media and NIH standards for the standard curve and iodination, Kus et al., Biochim. Biophys. Acta, 264:462–71 (1972). Blood was obtained by heart puncture at 10 a.m. just before sacrifice. Uteri from control rats showed that blood was removed throughout the estrous cycle in the various animals.
[b]Mean ± S.D.
[c]Administration described in legend to FIG. 2
[d]$p > 0.2$ versus that of the control value.
[e]$p < 0.001$ versus that of the control value.
[f]4-Nitroestrone 3-methyl ether (24 mg/kg) and/or tamoxifen (0.8 mg/kg) injected.
[g]$p < 0.002$ versus that of the control value.
[h]Administered according to the protocol of Fiebig et al., Oncology (Basel), 34:58–61 (1977: 1.2 mg Adriamycin per 0.6 ml of 0.9% NaCl solution per kg body weight on Days 1 to 3 and Days 14, 15, and 17, plus 20 mg 5-fluorouracil per 0.9 ml water (pH 9) per kg body weight on Days 1 to 4 and Days 14 to 17 (i.p.).

TABLE 2

Histopathological Characteristics of Tumors in Various Treatment Groups

| Treatment | Adenocarcinomas | Fibroadenomas | Total |
| --- | --- | --- | --- |
| None | 28 | 4 | 32 |
| Ovariectomy | 3 | 2 | 5 |
| 4-Nitroestrone 3-methyl ether | 3 | 12 | 15 |
| 4-Nitroestrone | 17 | 5 | 22 |
| Tamoxifen | 21 | 2 | 23 |
| Tamoxifen + 4-nitroestrone 3-methyl ether | 16 | 6 | 22 |
| Adriamycin + 5-fluorouracil | 15 | 2 | 17 |
| 17β-Estradiol 3-benzoate | 7 | 4 | 11 |

EXAMPLE 12

Effect of Time of Administration of Tumor-inhibiting Agent on Tumor Growth

Figure 3:
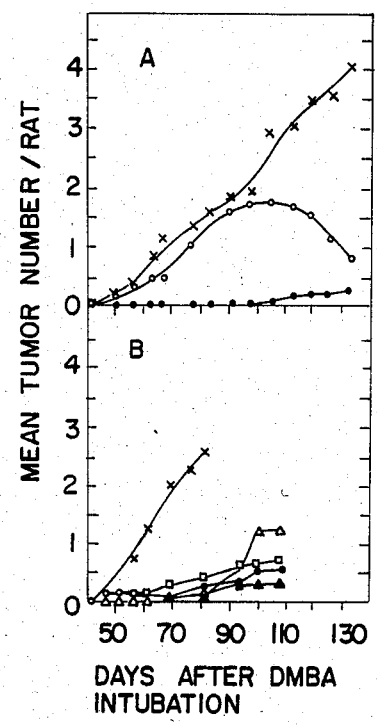

Each group of Sprague-Dawley rats (12 rats/group) was intubated with DMBA at 51 days of age. Rats were injected subcutaneously with 24 mg/kg of 4-nitroestrone 3-methyl ether or with 0.8 mg/kg of tamoxifen. Results are shown in FIG. 3A for the following treatments: injection of SSV only (X); 20 injections of 4-nitroestrone 3-methyl ester beginning 6 days following DMBA intubation (●); 25 injections of 4-nitroestrone 3-methyl ether beginning 92 days following DMBA intubation (o) and in FIG. 3B for these treatments; injection of sesame oil only (X); 10 injections with 4-nitroestrone 3-methyl ether 10 days prior to DMBA intubation (Δ); 10 injections with tamoxifen 10 days prior to DMBA intubation; (▲); 20 injections of 4-nitroestrone 3-methyl ether beginning 6 days following DMBA intubation (●); 20 injections of tamoxifen beginning 6 days following DMBA intubation (□)

These results show that 4-nitroestrone 3-methyl ether is equally effective on both precancerous cells and the established tumor.

EXAMPLE 13

Effect of 4-Nitroestrone 3-Methyl Ether on MXT Transplantable Murine Tumor (a) 4-Nitroestrone 3-methyl ether (NSC 321803) was evaluated for treatment of MXT mammary ductal carcinoma induced by urethane in accordance with Watson et al., *Cancer Research,* 37:3344 (1977).

Test drugs were administered intraperitoneally to female mice in which were implanted MXT murine mammary tumor cells (line 32/4/03) on the first day of testing. Other drugs evaluated simultaneously were tamoxifen (NSC 180973), mepitiostane (NSC 322366), and 3,4-[bis-(m-hydroxyphenyl]hexane (NSC 297170).

Figure 4:
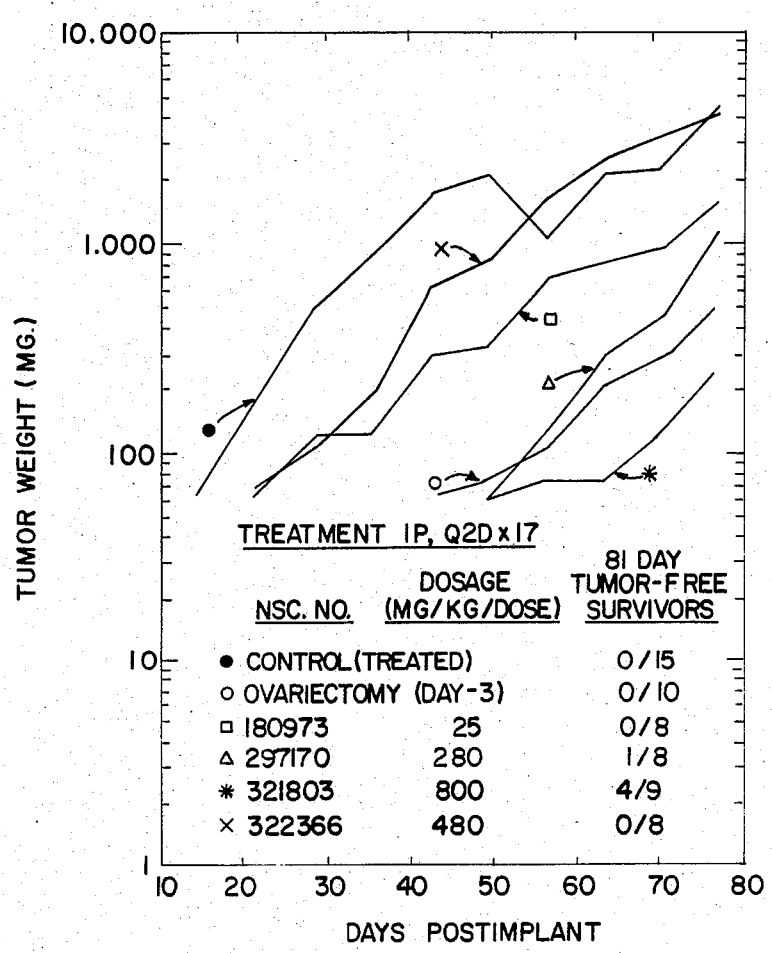
In FIG. 4 is shown the effect of 4-nitroestrone 3-methyl ether on the growth of ductal mammary carcinoma of the MXT type.

Results are shown in Table 3 and FIG. 4. It is apparent that 4-nitroestrone 3-methyl ether gives a higher number of tumor-free survivors than any of the other treatment protocols.

(b) Further evaluation at higher dosages were done by subcutaneous administration of 4-nitroestrone 3-methyl ether twice daily to mice for 30 days. Results are for evaluation 35 days after MXT tumor induction. The ovariectomized mice were ovariectomized six days before tumor implantation. In the table chart below, a T/C ratio to below 42% indicates significant antitumor activity and a T/C ratio below 10% of very high antitumor activity.

| Dose(mg/kg) | Survival | Tumor Weight (mg at 35 days) | | |
|---|---|---|---|---|
| | | Control | Treated | T/C in % |
| 1600 | 10/10 | 970 | 23 | 2.4 |
| 800 | 10/10 | 970 | 14 | 1.4 |
| 400 | 10/10 | 970 | 14 | 1.4 |
| OVX control | 10/10 | 970 | 19 | 1.9 |

These results show that 4-nitroestrone 3-methyl ether is highly effective in inhibiting the growth of MXT mammary tumors.

EXAMPLE 14

Evaluation of 4-Nitroestrone 3-O-($\gamma$-hydroxypropyl)Ether (ST; Y=NO$_2$, Z=CH$_3$CHOHCH$_2$—, X=H, R$_1$+R$_2$=O)

The hydroxypropyl compound was prepared by the method of McMahon et al., *J. Med. Pharm. Chem.,* 6:343 (1963).

Evaluation was done using female BDF$_1$ mice in which were implanted hormone dependent ductal carcinoma cells (MTX) on the first day of the experiment.

The experimental drugs were given orally or subcutaneously for 40 days, except that the 160 mg/kg dosage of the 3-O-($\gamma$-hydroxypropyl)ether was given for 16 days.

Tumors were bilaterally implanted sc into female mice on Day 0 of the experiment. Drug treatment began on Day 1.

Tumor weights were calculated from two dimensional measurements by the equation $(a \times b^2)/2$: $a=$ length; $b=$width in mm.

Tumors implanted into male BDF$_1$ mice served as controls (to demonstrate hormone dependence of the tumor.

In experiments with the 3-methyl ether, the mean tumor weight at the end of 40 days was 86 mg for male controls (1 of 5 was tumor free) and 1257 mg for female controls.

In experiments with the 3-O-($\gamma$-hydroxypropyl)ether, the mean tumor weight at Day 24 was 226 mg for male controls and 902 mg for female controls.

Results for the highest dosages are shown in Table 4 below.

No lethal toxicity or other untoward side effect was observed.

Both compounds were judged to have significant tumor inhibiting activity (T/C less than 42%) upon subcutaneous administration, as did the 3-O-(2-hydroxypropyl) compound administered orally.

TABLE 3

| Cage No. | NSC No. | Dose Mg/Kg | RT | Schedule | Lifespan (Days Post Implant) Median | Lifespan (Days Post Implant) Range | 0/0 ILS | Time (Days) to Reach: 500 MG | Time (Days) to Reach: 1000 MG | Delay (T-C) | PTR | Drug Deaths/ Total | Tumor Free Surv |
|---|---|---|---|---|---|---|---|---|---|---|---|---|---|
| 1 | Control (untreated) | | | | >81.0 | 46->81 | | 33.6 | 40.5 | | | | 0/10 |
| 2 | Control (ovariectomy, Day -3) | | | | >81.0 | 81->81 | | 71.5 | 77.9 | | | | 0.10 |
| 3 | Control (treated) | | | | >80.5 | 34->81 | | 29.2 | 35.9 | | | | 0/30 |
| 4 | 297170 | 280 | IP | Q 2D × 17 Day 1 | >81.0 | 22->81 | >0 | 68.9 | 69.8 | 36.8 | 60 | 1/10 | 1 |
| 5 | 297170 | 140 | IP | Q 2D × 17 Day 1 | >81.0 | 75->81 | >0 | 66.0 | 71.5 | 36.2 | 30 | 0/10 | 0 |
| 6 | 297170 | 70 | IP | Q 2D × 17 Day 1 | >81.0 | 81->81 | >0 | 62.6 | 71.8 | 34.6 | 40 | 0/10 | 1 |
| 7 | 297170 | 35 | IP | Q 2D × 17 Day 1 | >81.0 | 22->81 | >0 | 54.7 | 55.6 | 22.6 | 20 | 1/10 | 1 |
| 8 | 297170 | 17.5 | IP | Q 2D × 17 Day 1 | >81.0 | 74->81 | >0 | 41.3 | 51.5 | 13.8 | 20 | 0/10 | 1 |
| 9 | 321803 | 1600 | IP | Q 2D × 17 Day 1 | >81.0 | 3->81 | >0 | 68.0 | 75.3 | 39.1 | 70 | 2/10 | 3 |
| 10 | 321803 | 800 | IP | Q 2D × 17 Day 1 | >81.0 | 46->81 | >0 | 66.6 | 72.2 | 36.8 | 80 | 1/10 | 4 |
| 11 | 321803 | 400 | IP | Q 2D × 17 Day 1 | >81.0 | 34->81 | >0 | 71.6 | 73.2 | 39.8 | 70 | 1/10 | 2 |
| 12 | 321803 | 200 | IP | Q 2D × 17 Day 1 | >81.0 | 32->81 | >0 | 67.9 | 75.1 | 38.9 | 40 | 4/10 | 1 |
| 13 | 321803 | 100 | IP | Q 2D × 17 Day 1 | >81.0 | 24->81 | >0 | 66.8 | 66.5 | 34.1 | 40 | 2/10 | 1 |
| 14 | 322366 | 480 | IP | Q 2D × 17 Day 1 | >81.0 | 36->81 | >0 | 40.8 | 50.5 | 13.1 | 10 | 0/10 | 0 |
| 15 | 322366 | 240 | IP | Q 2D × 17 Day 1 | >81.0 | 44->81 | >0 | 30.6 | 35.9 | 0.7 | 0 | 0/10 | 0 |
| 16 | 322366 | 120 | IP | Q 2D × 17 Day 1 | >74.0 | 46->81 | >-9 | 29.3 | 36.8 | 0.5 | 10 | 0/10 | 0 |
| 17 | 322366 | 60 | IP | Q 2D × 17 Day 1 | >81.0 | 52->81 | >0 | 38.1 | 44.6 | 8.8 | 20 | 0/10 | 0 |
| 18 | 322366 | 30 | IP | Q 2D × 17 Day 1 | 76.5 | 46->81 | -5 | 35.3 | 42.4 | 6.3 | 0 | 0/10 | 0 |
| 19 | 180973 | 150 | IP | Q 2D × 17 Day 1 | 25.0 | 8->81 | -69 | 63.2 | UE | 30.6 | 0 | 8/10 | 0 |
| 20 | 180973 | 100 | IP | Q 2D × 17 Day 1 | 64.0 | 6->81 | -21 | 47.9 | 54.9 | 18.8 | 0 | 5/10 | 0 |
| 21 | 180973 | 50 | IP | Q 2D × 17 Day 1 | >81.0 | 20->81 | >0 | 60.9 | 60.9 | 28.3 | 50 | 2/10 | 1 |
| 21 | 180973 | 25 | IP | Q 2D × 17 Day 1 | >81.0 | 55->81 | >0 | 51.7 | 60.1 | 23.3 | 30 | 0/10 | 0 |

EXAMPLE 15

Preparation of a Longlasting Troche

Troches (1500), each weighing 750 mg, were formulated as follows:

| Ingredient | Grams |
|---|---|
| (a) 3-Methoxy-4-nitroestrone | 15.0 |
| (b) Pectin | 370.0 |
| (c) Gelatin | 370.0 |
| (d) Sodium carboxymethylcellulose | 370.0 |

The diol was mixed with approximately 10 gm. of pectin. The remainder of the pectin and other ingredients were added and mixed thoroughly. The resulting mixture was compressed into capsule-shaped troches, each of which contained 10 mg of 3-methoxy-4-nitroestrone.

TABLE 4

| | Dosage mg/Kg dose | Drug Route | Total Dose* mg/Kg | Tumor Weight in mg (mean) | | T/C Value day 40 |
|---|---|---|---|---|---|---|
| | | | | Control (C) day 40 | Treated (T) day 40 | |
| 4-NO$_2$—estrone 3-methyl ether | 80 | sc | 3200 | 1257 | 215 | 17% |
| | 80 | oral | 3200 | 1257 | 909 | 72% |
| 4-NO$_2$—estrone 3-O—(η-hydroxypropyl) ether | 80 | oral | 3200 | 1257 | 376 | 30% |
| | 160 | sc | 2560 | 2709* | 150* | 6%* |

\* Day 39 measurement

EXAMPLE 16

Preparation of a Hard Candy Lozenge

The following formulation can be used to prepare approximately 9,000 lozenges weighing 5.0 grams each.

| Ingredient | Weight |
|---|---|
| (a) 3-O—(η-Hydroxypropyl)-4-nitroestrone | 90 gms. |
| (b) Sodium cyclamate | 450 gms. |
| (c) Saccharin sodium | 45 gms. |
| (d) Cetyl diethyl benzyl ammonium chloride | 27 gms. |
| (e) Benzocaine | 45 gms. |

-continued

| Ingredient | Weight |
|---|---|
| (f) Granular sugar | 28 gms. |
| (g) Liquid glucose (43°) | 16.7 kgs. |
| (h) Sour orange flavor q.s. | |
| Wild cherry flavor q.s. | |

The granular sugar is placed into a pre-cook kettle with 14 liters of water. The mixture is brought to a boil and the sodium cyclamate is added and dissolved with stirring. Glucose is added and the mixture brought to a predetermined temperature of 135° C.

The composition is transferred to a continuous vacuum cooker and reduced to a proper consistency for a candy base, to which the remaining ingredients are added with stirring. The mixture is thoroughly kneaded and a continuous rope formed. Lozenges weighing about 5.0 gm. each and containing about 10.0 mg. of the hydroxyalkyl estrone are cut from the rope, packaged and distributed in any convenient manner.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

We claim:

1. A method for inhibiting the growth of MXT murine ductal carcinoma comprising administering to an animal being treated a compound of the formula

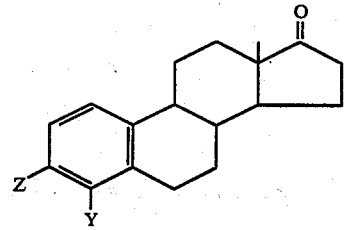

wherein Z is γ-hydroxypropyl and Y is nitro, in admixture with a pharmacologically and physiologically acceptable carrier, in an amount sufficient to inhibit the growth of the ductal carcinoma.

2. The method of claim 1 wherein the compound is administered subcutaneously.

3. The method of claim 1 wherein the compound is administered orally.

* * * * *